United States Patent [19]
Barberich et al.

[11] Patent Number: 5,919,827
[45] Date of Patent: Jul. 6, 1999

[54] METHOD FOR TREATING ASTHMA USING OPTICALLY PURE R(-) SALMETEROL

[75] Inventors: Timothy J. Barberich, Concord, Mass.; James W. Young, Palo Alto, Calif.

[73] Assignee: Sepracor Inc., Marlborough, Mass.

[21] Appl. No.: 08/992,376

[22] Filed: Dec. 17, 1997

Related U.S. Application Data

[63] Continuation of application No. 08/430,746, Apr. 28, 1995, abandoned, which is a continuation of application No. 08/008,526, Jan. 25, 1993, abandoned, which is a continuation-in-part of application No. 07/551,622, Jul. 11, 1990, abandoned.

[51] Int. Cl.$^6$ .................................................. A61K 31/135
[52] U.S. Cl. ............................................. 514/651; 514/649
[58] Field of Search ...................... 514/651, 649

[56] References Cited

U.S. PATENT DOCUMENTS 4,992,474  2/1991  Skidmore et al. ....................... 514/653

FOREIGN PATENT DOCUMENTS 0422889  4/1991  European Pat. Off. .
2140800  12/1984  United Kingdom .

OTHER PUBLICATIONS

J. Morley et al., Effects of (+) and Racemic Salmutamol on Airway Responses in the Guinnea–Pig, BR. *J. Pharmaca.*, 104, Proc. Supp. (1991).

Larsson, Chem. Abst. 114(3): 1694lr; "Long–term Studies on Long Acting Sympathomimetics", *Lung 168* (Suppl), 22–24 (1990).

Johnson, Chem. Abst. 114(3): 16944u: "The Pharmacology of Salmeterol", *Lung 168* (Suppl.) 115–119 (1990).

Chem. Abst. 114 (7): 55571q; Brittain, "Approaches to a Long–Acting, Selective beta$_2$–adrenoceptor Stimulant", *Lung 168* (Suppl.), 111–114 (1990).

World Patent Index Acc. No.: 84–264874/43; DE 3414752, Oct. 18, 1984, Skidmore et al., New Phenyl Amino Ethanol Derivative.

Jamali et al., "Enantioselective Aspects of Drug Action and Disposition: Therapeutic Pitfalls", *J. Pharma. Sci.* 78(9), 695–711 (1989).

*Primary Examiner*—William R. A. Jarvis
*Attorney, Agent, or Firm*—Heslin & Rothenberg, P.C.

[57]  ABSTRACT

The optically pure R(-) isomer of salmeterol, which is substantially free of the S(+) isomer, is a potent bronchodilator for relieving the symptoms associated with asthma in individuals. A method is disclosed utilizing the optically pure R(-) isomer of salmeterol for treating asthma while minimizing toxicity and other side effects associated with salmeterol.

8 Claims, No Drawings

METHOD FOR TREATING ASTHMA USING OPTICALLY PURE R(−) SALMETEROL

RELATED APPLICATIONS

This application is a continuation of Ser. No. 08/430,746, filed Apr. 28, 1995, now abandoned, which is a continuation of Ser. No. 08/008,526, filed Jan. 25, 1993, now abandoned, which is a Continuation-In-Part of U.S. Ser. No. 07/551,622 filed Jul. 11, 1990, now abandoned. The teachings of this application are incorporated herein by reference.

BACKGROUND

Salmeterol, 4-hydroxy-$\alpha^1$-[[6-(4-phenylbutoxy) hexyl]amino]methyl-1,3-benzenedimethanol, is a drug belonging to the general class of beta-adrenergic compounds. The prime action of beta-adrenergic drugs is to stimulate adenyl cyclase, the enzyme which catalyzes the formation of cyclic-3',5'-adenosine monophosphate (AMP) from adenosine triphosphate (ATP). The cyclic AMP formed mediates the cellular responses. Salmeterol acts selectively on $beta_2$-adrenergic receptors to relax smooth muscle tissue, for example, in the bronchial system. Salmeterol is most commonly used to treat bronchial spasms associated with asthma. Its activity is similar to that of albuterol which is the active component in well-known commercial bronchodilators such as Proventil and Ventolin. However, the beneficial effects of salmeterol are longer lasting than those of albuterol. Thus, use of salmeterol is more desirable than use of albuterol.

The form in which salmeterol is presently used is a racemic mixture. That is, it is a mixture of optical isomers, called enantiomers. Enantiomers are structurally identical compounds which differ only in that one isomer is a mirror image of the other and the mirror images cannot be superimposed. This phenomenon is known as chirality. Most biological molecules exist as enantiomers and exhibit chirality. Although structurally identical, enantiomers can have profoundly different effects in biological systems: one enantiomer may have a specific biological activity while the other enantiomer has no biological activity or may have an entirely different form of biological activity.

SUMMARY OF THE INVENTION

The present invention relates to a method of treating bronchial disorders, such as asthma, in an individual, by administering to the individual an amount of optically pure R(−) salmeterol which is active in bronchial tissue and is sufficient to reduce bronchial spasms associated with asthma while minimizing side effects associated with salmeterol as it is now given. The method is particularly useful in treating asthma while reducing side effects of salmeterol as it is now given, such as central nervous system stimulatory effects and cardiac arrhythmia. In these applications, it is important to have a composition which is a potent broncho-dilator but does not produce the adverse side effects of many beta-adrenergic drugs. A composition containing the pure R(−) isomer of salmeterol is particularly useful for this application because this isomer exhibits these desired characteristics. The present method provides a safe, effective method for treating asthma while reducing undesirable side effects, such as hypersensitivity, tolerance (tachyphylaxis), tremor, nervousness, shakiness, dizziness and increased appetite, and particularly, cardiac arrhythmia, typically associated with beta-adrenergic drugs. In children, side effects such as excitement, nervousness and hyperkinesia are reduced when the pure isomer is administered. Because R(−) salmeterol can be administered at lower doses than racemic salmeterol, there is also a reduced likelihood of toxicity. For example, an equipotent R(−) salmeterol dose exhibits lower toxicity to the renal and hepatic system as evidenced by less deviation from normal in kidney and liver function tests.

DETAILED DESCRIPTION OF THE INVENTION

The present invention relies on the bronchodilation activity of the R(−) enantiomer of salmeterol to provide relief from bronchial disorders, while simultaneously reducing toxicity and other undesirable side effects, such as hypersensitivity, tachyphylaxis, central nervous system stimulatory effects and cardiac disorders, commonly experienced by salmeterol users. In the present method, the optically pure R(−) isomer of salmeterol, which is substantially free of the S(+) enantiomer, is administered alone, or in combination with one or more other drug(s) in adjunctive treatment, to an individual in whom asthma relief (e.g., relief from bronchial spasms, shortness of breath) is desired. The optically pure R(−) isomer of salmeterol as used herein refers to the levorotatory optically pure isomer and to any biologically acceptable salt or ester thereof. The terms "optically pure" or "substantially free of the S(+) enantiomer" as used herein means that the composition contains at least 90% by weight of the R(−) isomer of salmeterol and 10% by weight or less of the S(+) isomer. Optically pure salmeterol is readily obtainable by methods known to those of skill in the art, for example, by synthesis from an optically pure intermediate.

In the present method, the R(−) isomer of salmeterol is administered to an individual who has asthma. For example, R(−) salmeterol is administered to an individual after onset of asthma to reduce breathing difficulty resulting from asthma. In another embodiment, optically pure R(−) salmeterol is administered prophylactically, that is, before the bronchiospasm begins in an asthma attack, to prevent its occurrence or to reduce the extent to which it occurs.

In the present method, R(−) salmeterol can be administered by inhalation, by subcutaneous or other injection, orally, intravenously, topically, parenterally, transdermally, rectally or via an implanted reservoir containing the drug. The form in which the drug will be administered (e.g., inhalant, powder, tablet, capsule, solution, emulsion) will depend on the route by which it is administered. The drug also can be administered in sustained-release dosage forms, either orally or topically, e.g. by transdermal delivery from a topically applied patch or similar device. The quantity of the drug to be administered will be determined on an individual basis, and will be based at least in part on consideration of the individual's size, the severity of the symptoms to be treated and the result sought. In general, quantities of optically pure R(−) salmeterol sufficient to reduce the symptoms of asthma will be administered. The actual dosage (quantity administered at a time) and the number of administrations per day will depend on the mode of administration, for example, by inhaler, nebulizer, topical or oral administration. About 25 mcg to about 50 mcg of the optically pure R(−) isomer of salmeterol given by inhalation one or more times per day will be adequate in most individuals to produce the desired bronchodilation effect. For oral administration, e.g., tablet or syrup, a dose of about 1 mg to about 8 mg two to four times daily is administered to produce the desired effect.

In the method of the present invention, the optically pure R(−) isomer of salmeterol can be administered together with one or more other drug(s). For example, an antiasthmatic drug such as theophylline or terbutaline, or an antihistamine or analgesic such as aspirin, acetaminophen or ibuprofen, can be given with or in close temporal proximity to administration of optically pure, R(−) salmeterol. The two (or more) drugs (i.e., the optically pure active isomer of salmeterol and another drug) can be administered in one composition or as two separate entities. For example, they can be administered in a single capsule, tablet, powder, or liquid, etc. or as individual compounds. The components included in a particular composition, in addition to optically pure salmeterol and another drug or drugs, are determined primarily by the manner in which the composition is to be administered. For example, a composition to be administered in inhalant form can include, in addition to the drug(s), a liquid carrier and/or propellant. A composition to be administered in tablet form can include a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the combination of drugs and, optionally, an emulsifying agent, a flavoring agent and/or a coloring agent.

In general, according to the method of the present invention, the optically pure R(−) isomer of salmeterol, alone or in combination with another drug(s), is administered to an individual periodically as necessary to reduce symptoms of asthma.

The present composition and method provide an effective treatment for asthma while minimizing or eliminating tachyphylaxis, hypersensitivity, toxicity and other undesirable side effects associated with salmeterol use as now given. These side effects include central nervous system effects, such as tremor, nervousness, shakiness, dizziness and increased appetite, and cardiac effects, such as cardiac arrhythmia. In children, side effects such as excitement, nervousness and hyperkinesia are reduced when the pure isomer is administered.

EXEMPLIFICATION

The invention is further defined by reference to the following procedures describing the pharmacological characterization of the compositions of the present invention and by reference to the following method of administering the compositions of the present invention. It will be apparent to those skilled in the art that many modifications, both to materials and methods, may be practiced without departing from the purpose and interest of this invention.

Pharmacological Characterization Procedures

PROCEDURE 1

β-Adrenergic Receptor Phosphorylation by β-Adrenoreceptor Kinase

Reconstituted β-adrenergic receptor is incubated with β-adrenoreceptor kinase in a buffer containing 20 mM Tris-HCl, pH 7.5, 2 mM EDTA, 20 mM NaCl, 6 mM MgCl$_2$, 6 mM sodium phosphate, 0.5 mM ascorbic acid 60 $\mu$M [-γ-$^{32}$P]ATP at 30° C. The incubations also contain varying concentrations of one of the following: buffer (control) (−)-isoproterenol, R(−) salmeterol, S(+) salmeterol or racemic salmeterol. The incubations are stopped by the addition of SDS sample buffer followed by electrophoresis on 10% homogeneous polyacrylamide gels. Stoichiometries of phosphorylation are determined by cutting and counting the dried gel as described in Benovic J. L. et al., *J. Biol. Chem.* 9026–9032 (1987).

PROCEDURE 2

Purification of Component Proteins

The β-adrenergic receptor from hamster lung is purified to >95% homogeneity by sequential affinity chromatography and high performance liquid chromatography as described in Benovic et al., *Biochemistry* 23, 4510–4518 (1984). The stimulatory guanine nucleotide regulatory protein is purified from membranes derived from bovine cerebral cortex. The membranes, solubilized with 1% cholate, are centrifuged and the resulting supernatant chromatographed on DEAE-Sephacel, Ultrogel AcA34, octyl-Sepharose, and hydroxyapatite, with a final step on DEAE-Sephacel, as adapted from Strittmater et al., *Proc. Natl. Acad. Sci.* 77, 6344–6348 (1980). The resulting protein should be 50–90% pure by Coomassie Blue staining of polyacrylamide gels. The catalytic moiety of adenylate cyclase is solubilized from bovine caudate with sodium cholate and isolated from the other components of the system by Sepharose 6B chromatography as described in Strittmater et al., supra. β-Adrenoreceptor kinase is purified from bovine cerebral cortex. The tissue is homogenized, and the resulting high speed supernatant fraction is precipitated with 13–26% ammonium sulfate. This material is then chromatographed on Ultrogel AcA34, DEAE-Sephacel, and CM-Fractogel. The preparations used should be 10–20% pure as judged by Coomassie Blue staining of SDS-polyacrylamide gels.

Assay for Adenylate Cyclase Activity

The co-reconstitution of the purified proteins is carried out as described in Cerione et al., *J. Biol. Chem.* 259 9979–9982 (1984). The pelleted proteins are incubated for 15 min. at 37° C. in 30 mM Tris-HCl, pH 7.5 containing 1 mM ATP, 2 $\mu$Ci of [α-$^{32}$P]ATP 0.14 mM cAMP, 100 mM sucrose, 0.4 mM dithiothreitol, 2.8 mM phosphoenol pyruvate, 5.2 $\mu$g/mL pyruvate kinase, 10 $\mu$g/ml of myokinase, 5 mM MgCl$_2$, and varying concentrations of racemic salmeterol, R(−) salmeterol and S(+) salmeterol (total volume=0.5 mL). The reaction is stopped by the addition of 0.25 mL 2% sodium dodecylsulfate containing 40 mM ATP and 1.4 mM cAMP at pH 7.5. Water (0.5 mL) is added to each reaction tube and the contents placed on a Dowex 50AG WX4 resin. The eluate from the columns plus two successive water washes (1.0 mL) are discarded. The columns are then eluted with 3 mL water and the eluates collected in test tubes. Each fraction is diluted with 0.2 mL of 1.5 M imidazole HCl, pH 7.2. The tubes from each concentration (run in triplicate) are combined and decanted into columns containing 0.6 g neutral alumina that has been previously washed with 0.1 M imidazole HCl, pH 7.5. The eluate is collected in scintillation vials containing 12 mL Aquasol®. After the columns are completely drained, they are washed with an additional 1 mL of 0.1 M imidazole HCl, pH 7.5 which is collected in the same scintillation vials. The concentration of $^{32}$P-cAMP is determined in each sample.

PROCEDURE 3

β-Selectivity Studies

Albino, female guinea pigs, weighing 300 to 500 g, are killed by trauma to the head. The tissues are removed, trimmed of excess tissue and suspended in water-jacketed (37–38° C.) 10-ml tissue baths containing a physiologic salt solution of the following composition: 118 mM NaCl, 4.7 mM KCl, 2.5 mM CaCl$_2$.2H$_2$O, 0.5 mM MgCl$_2$.6H$_2$O, 1 mm NaH$_2$PO$_4$.H$_2$O, 25 mM NaHCO$_3$, and 11 mM glucose. The tissue baths and stock salt solution are aerated with a mixture of oxygen (95%) and carbon dioxide (5%). Mechanical responses are recorded on a polygraph via force displacement transducers.

Cumulative dose-response effects of the agonists are obtained by increasing the concentrations by a factor of about 3 while the previous dose remains in contact with the tissue. Each concentration is added only after the effects of the previous concentration reach maximum and remain constant. Final maximum responses are taken to be the effects occurring when a 3-fold increase in agonist concentration fails to further elicit a response. The time required to obtain complete dose-response effects varies with the agonist employed. All other compounds are added to the bath in a volume of 0.1 ml and allowed to interact with the tissue for fixed periods of time.

Isolated Right Atria

Spontaneous atrial contractions are recorded together with atrial rate which is monitored with tachographs to aid in determining when maximum responses occur after a given concentration of agonist. The amount of tension exerted on each atrium is the maximum needed to obtain a pen deflection of about 0.5 cm/beat at the highest preamplifier sensitivity without recording background noise. Each tissue is allowed to equilibrate for 1 hour prior to addition of any drug, and washings are made at 15-minute intervals during this period. For construction of dose-response curves, the initial rate (beats per minute) is taken as that occurring just prior to beginning cumulative drug addition.

Isolated Treacheal Strips

Trachea are cut in spiral fashion, each turn separated by 3 to 4 cartilage segments. Each strip is approximately halved and each half mounted in a tissue bath. Resting tension is adjusted to 5 g and maintained at that level during equilibration and drug incubation periods. Strips are allowed to equilibrate for 2 hours prior to addition of any drug, and washings are made at 15-minute intervals during this period. Relaxation produced by beta receptor agonists is studied after partial contraction with $3 \times 10^{-7}$ M carbachol. As previously determined, this concentration produces a degree of contraction representing approximately 30% of the maximum capable of being produced by this agonist. The contraction reaches maximum in 10 to 15 minutes and remains constant for at least 1 hour. In order to keep drug contact periods constant, cumulative addition of beta receptor agonists is begun 15 minutes after addition of carbachol to the bath.

DRUG ADMINISTRATION BY ORAL INHALATION

The metered dose dispenser contains micronized (R) salmeterol in suspension. Each actuation delivers 25 μg of (R) salmeterol from the mouthpiece. Each canister provides about 120 inhalations. The chemical composition of a metered dose is provided below in Table 1.

TABLE 1

| Formula | Quantity Contained in Each Metered Dose Dispenser 7.5 mL (10.5 g) Canister |
|---|---|
| (R) Salmeterol | 3.0 mg |
| Trichloromonofluoromethane | 5.16 g |
| Dichlorodifluoromethane | 5.16 g |
| Sorbitan Trioleate | 0.105 g |

Equivalents

Those skilled in the art will recognize, or be able to ascertain, using no more than routine experimentation, many equivalents to the specific embodiments of the invention described herein. Such equivalents are intended to be encompassed in the scope of the following claims.

We claim:

1. A method of treating asthma in an individual with salmeterol, while reducing toxicity and other side effects associated with salmeterol, comprising administering to the individual a quantity of an optically pure R(−) isomer of salmeterol sufficient to result in bronchodilation, said R(−) isomer being substantially free of its S(+) isomer.

2. A method of claim 1 wherein the amount of the R(−) isomer of salmeterol is greater than approximately 90% by weight.

3. A method of claim 2 wherein the amount of the R(−) isomer of salmeterol is greater than 99% by weight.

4. A method of claim 1 comprising administering to the individual by inhalation from approximately 25 mcg to approximately 50 mcg of the R(−) isomer of salmeterol per dose.

5. A method of claim 1 comprising orally administering to the individual from approximately 1 mg to approximately 8 mg of the R(−) isomer of salmeterol one to four times daily.

6. A method of treating asthma in an individual with salmeterol, while reducing side effects associated with salmeterol, comprising administering to the individual a quantity of an optically pure R(−) isomer of salmeterol sufficient to result in bronchodilation and at least one additional drug.

7. A method of claim 6 wherein the additional drug is selected from the group consisting of bronchodilators, antihistamines and analgesics.

8. A method of claim 7 wherein the analgesic is selected from the group consisting of aspirin, acetaminophen and ibuprofen.

* * * * *